United States Patent [19]

Saito et al.

[11] 4,263,449

[45] Apr. 21, 1981

[54] PROCESS FOR PRODUCING ALCOHOLS

[75] Inventors: Toshihiro Saito; Yukihiro Tsutsumi; Shoji Arai, all of Shin-nanyo, Japan

[73] Assignee: Toyoda Soda Manufacturing Co., Ltd., Shin-nanyo, Japan

[21] Appl. No.: 133,438

[22] Filed: Mar. 24, 1980

[30] Foreign Application Priority Data

May 15, 1979 [JP] Japan ................... 54-58580

[51] Int. Cl.³ ............... C07C 67/38; C07C 29/16; C07C 31/20; C07C 41/01
[52] U.S. Cl. .................. 560/263; 568/648; 568/678; 568/831; 568/862; 568/882; 568/883
[58] Field of Search ............ 568/882, 862, 678, 831, 568/648, 883; 560/263

[56] References Cited

U.S. PATENT DOCUMENTS

| | | | |
|---|---|---|---|
| 2,636,903 | 4/1953 | Mertzweiller | 568/882 |
| 2,669,589 | 2/1954 | Catterall et al. | 568/882 |
| 2,743,302 | 4/1956 | Gwynn et al. | 568/882 |
| 2,843,632 | 7/1958 | Gwynn et al. | 568/882 |
| 3,182,090 | 5/1965 | Mertzweiller et al. | 568/882 |
| 3,636,034 | 1/1972 | Ohsuml et al. | 568/882 |
| 3,819,727 | 6/1974 | Ferrari et al. | 568/882 |
| 3,821,311 | 6/1974 | Hughes et al. | 568/882 |
| 4,083,882 | 4/1978 | Taylor et al. | 568/862 |

FOREIGN PATENT DOCUMENTS

| | | | |
|---|---|---|---|
| 39-28748 | 12/1964 | Japan | 568/882 |
| 41-14738 | 8/1966 | Japan | 568/882 |
| 42-6168 | 3/1967 | Japan | 568/882 |

OTHER PUBLICATIONS

Brown et al., "J. Chem. Soc.(A)" 1970, pp. 2753-2764.

Primary Examiner—Joseph E. Evans
Attorney, Agent, or Firm—Oblon, Fisher, Spivak, McClelland & Maier

[57] ABSTRACT

An alcohol is produced from a compound having an alkenyl group by a hydroformylation of said compound having an alkenyl group in a substantially water immiscible solvent in the presence of a hydroformylation catalyst which is soluble in said solvent and a hydrogenation of the reaction mixture in the presence of a hydrogenation catalyst.

Water is added at a ratio of 0.5 to 30 times by weight base on an aldehyde produced by said hydroformylation before said hydrogenation, and an organic phase containing the hydroformylation catalyst component is separated from a water phase containing the alcohol produced by said hydrogenation and said organic phase is recycled into said hydroformylation.

The compound having an alkenyl group is an aliphatic olefin, a hydroxyolefin, and olefin ether or an olefin ester and the corresponding saturated alcohol having one more carbon atom is produced.

8 Claims, No Drawings

PROCESS FOR PRODUCING ALCOHOLS

BACKGROUND OF THE INVENTION

1. Field of the Invention

The present invention relates to a process for producing an alcohol by a hydroformylation and a hydrogenation of an olefin.

2. Description of the Prior Arts:

It has been well-known that an alochol is produced by reacting an olefin with carbon monoxide and hydrogen by a hydroformylation and reducing the resulting aldehyde by a hydrogenation as an effective method of a production of an alochol, for example, a product of butanols from propylene (Yuki Gosei Kyokai Shi Vol. 35, No. 8, page 683 (1977)).

A carbonyl complex of the group VIII metal has been used as a catalyst in a hydroformylation of an olefin. When a rhodium catalyst such as a catalyst of a rhodium complex and excess of an organic tertiary phosphine is used, the catalyst has high stability and high catalytic activity whereby the hydroformylation can be carried out under mild conditions of a low temperature and a low pressure, and a yield of a straight chain aldehyde is high by using an $\alpha$-olefin and they are remarkably advantageous in an industrial process as disclosed in J. Falbe, "Carbon Monoxide in Organic Synthesis" page 16 (1970).

The present invention relates to a process for producing an alochol by a hydrogenation of an aldehyde derived from an olefin by a hydroformylation.

In the conventional process for producing an alcohol from an olefin, an aldehyde produced by a hydroformylation of an olefin is separated from the reaction mixture obtained by the hydroformylation to eliminate the catalyst and by-products and then, it is used in the hydrogenation.

The reaction mixture contains the object product which may be easily cause a trouble such as a polymerization, and various kinds of by-products whose reactivities are unknown and the expensive hydroformylation catalyst such as rhodium component. Therefore, it is understood that disadvantageous results such as a decrease of an yield, an increase of a content of impurities and a loss of the catalyst are caused if the reaction mixture itself is used in the next step. Therefore, various processes for separating the object aldehyde from the catalyst such as a distillation or an extraction have been developed and proposed (for example, Japanese Unexamined Patent Publication No. 29412/1976).

Thus, these separations have certain disadvantages. For example, the distillation method has disadvantages that a thermal deterioration of the object aldehyde caused by low thermal stability; sometimes, excess of equipments caused by a high boiling point of the object aldehyde and an inactivation and a loss of the catalyst in the extraction method and they are not satisfactory. Thus, the hydroformylation of an olefin and a hydrogenation of the object aldehyde have been known, however, it has not been industrially worked, beside special exceptional cases, to produce an alcohol from an olefin by one continuous process.

SUMMARY OF THE INVENTION

It is an object of the present invention to overcome said disadvantages in an industrial processes of a low yield, a polymerization, an increase of impurities and a loss of an expensive catalyst.

The foregoing and other objects of the present invention have been attained by carrying out a hydroformylation of an olefin in a substantially water immiscible solvent in the presence of a hydroformylation catalyst which is soluble in said solvent; adding water at a ratio of 0.5 to 30 times by weight based on the resulting aldehyde to the reaction mixture; carrying out a hydrogenation in the presence of a hydrogenation catalyst; separating an organic phase containing the hydroformylation catalyst component from a water phase containing the object alcohol; recycling the organic phase into the hydroformylation; and recovering the object alcohol from the water phase.

DETAILED DESCRIPTION OF THE PREFERRED EMBODIMENTS

The characteristic effects of the present invention are as follows.

(1) A separation of the interemediate is not carried out whereby the process is simplified to save costs for equipments and utilities.

(2) The hydrogenation is carried out under mild conditions without any separation of the intermediate whereby a deterioration and a loss of the aldehyde as the intermediate which is thermally unstable are not caused to give high yield of the alcohol.

(3) Although a large loss of the catalyst is caused by the separation of the intermediate by the conventional process, the loss of the catalyst is remarkably decreased by the separation of the catalyst after the hydrogenation in the present invention. The rhodium catalyst is expensive and accordingly, this is remarkably advantageous in an industrial process (see Example 1 and Reference 2).

(4) Although a large portion of the aldehyde is recyled in the solution of the catalyst by the conventional extraction of the intermediate with water, no aldehyde is included in the solution of the catalyst recycled after the hydrogenation to be advantageous in view of equipments and utilities in the present invention (See Example 1 and Reference 2).

(5) A reaction velocity of the hydrogenation can be controlled as desired by the addition of more than 0.5 time by weight of water based on the aldehyde as the intermediate.

(6) The organic solvent phase separated by a phase separation of the hydrogention can be recycled as the solution of the catalyst into the hydroformylation. As the process of Example 2, even though the recycling is repeated, the catalytic activity of the solution of the catalyst is not lowered.

(7) On the other hand, the alcohol as the object product can be obtained from the water phase obtained by the phase separation after the hydrogenation by the conventional method such as a distillation. The contamination of the hydroformylation catalyst into the water phase is remarkably small to be negligible.

Thus, the present invention is to provide an industrial process for producing an alcohol from an olefin by the hydroformylation and the hydrogenation. For example, butanediol can be economically produced from allyl alcohol.

The process of the present invention will be described in detail.

The alcohols produced by the process of the present invention include monohydric alcohols such as propanol and butanol; polyhydric alcohols such as diols and triols.

The compound having an alkenyl group used as the starting materials have 2 to 20 carbon atoms and include aliphatic olefins such as ethylene, propylene and cyclohexene; hydroxy olefins such as ally alcohol and 2-methyl-1-butene-4-ol; olefin ethers such as ethyl vinyl ether and allyl phenyl ether; olefin esters such as allyl acetate, 1,4-diacetoxy-2-butene, etc.

The hydroformylation of the olefin is carried out by using a catalyst.

The solvents used in the hydroformylation should be substantially inert in both of the hydroformylation and the hydrogenation and dissolve the hydroformylation catalyst and the compound having an alkenyl group and are not substantially miscible to water. Suitable solvents include aromatic hydrocarbons such as benzene, toluene and xylene; ethers such as dipropyl ether, dibutyl ether and anisole; and esters such as ethyl acetate, ethyl benzoate and di-2-ethylhexyl phthalate.

The hydroformylation catalysts should be stable in the hydrogenation and water immiscible or sparingly miscible. In view of a catalytic activity, a stability and a solubility to the solvent, it is especially preferable to use rhodium complexes such as $HRh(CO)(PR_3)_3$ or $HRh(CO)_2(PR_3)_2$ wherein $PR_3$ represents an organic tertiary phospine; R represents a $C_2$–$C_{20}$ alkyl group or a $C_6$–$C_{20}$ aryl group, in the hydroformyation.

The phospines are preferably triaryphospines such as triphenylphosphine and tritolyphosphine, in view of a catalytic activity, a stability, a solubility to the solvent and water and a cost.

When a rhodium complex is used, it is enough to incorporate at a concentration of 0.1 to 100 mg. atom as Rh in 1 liter of the reaction mixture of the hydroformylation. On the other hand, it is preferable to incorporate excess of the organic tertiary phosphine to the rhodium component in the reaction system in view of a selectivity, a stability and life of the catalyst. Thus, the organic tertiary phospine is incorporated at a molar ratio of 5 to 200 based on Rh of the catalyst.

In the hydroformylation, a molar ratio of hydrogen to carbon monoxide can be selected depending upon the compound having an alkenyl group as the starting material, a desired selectivity and a reaction velocity of the reaction and is usually in a range of 1/10 to 10/1. An inert gas such as nitrogen can be incorporated in the reaction system. The reaction pressure is in a range of 0 to 50 kg/cm$^2$(gauge) and the reaction temperature is in a range of an ambient temperature to 200° C.

The reaction mixture obtained by the hydroformylation is fed to the hydrogenation step after purging carbon monoxide and adding water without a separation of the aldehyde from the mixture. Water is incorporated at a ratio of 0.5 to 30 times preferably 1.0 to 20 times by weight based on the aldehyde in the reaction mixture. When water is not added or added at a quite small ratio, the reaction velocity of the hydrogenation is too slow, whereby side-reactions such as a condensation of the aldehyde is remarkably resulted and a recovery efficiency of the alcohol is lower in the separation. On the other hand, water can be added at higher ratio without adverse effect to the hydrogenation, however, a large equipment and energy are required for separating the object alcohol and a loss of the hydroformylation catalyst in uneconomically too much.

The hydrogenation can be carried out under a pressure of hydrogen in the presence of the hydrogenation catalyst after the addition of water. The hydrogenation catalysts can be the known catalysts such as nickel, cobalt, palladium, platinum and ruthenium and preferably Raney nickel or Raney cobalt in vies of a catalytic activity and economical problem. An amount of the catalyst is not critical and is selected depending upon a reaction velocity and an elimination of heat.

In the case of the Raney nickel catalyst, it is preferably to incorporate it at a ratio of 1 to 30 wt.% based on the aldehyde. The hydrogen pressure is not critical. When the hydrogen pressure is too low, the reaction velocity is too low whereas when it is to high, the special equipment is uneconomically required. The hydrogen pressure is preferably in a range of 5 to 100 kg/cm$^2$ (gauge).

When the temperature of the hydrogenation is too high, the production of the by-products is highly resulted over the thermal stability whereas when it is too low, the reaction velocity is too low. Thus, the reaction temperature is usually in a range of 20 to 200° C. preferably 40 to 150° C.

The reaction mixture obtained by the hydrogenation is kept in stand-still after purging hydrogen gas to carry out the phase separation into the organic phase and the water phase. The hydrogenation catalyst is separated by a filtration from the reaction mixture before the phase separation or the organic phase or the water phase after the phase separation. The separation is preferably carried out in the absence of oxygen, for example, in an inert gas atmosphere such as hydrogen and/or nitrogen or helium. The separated organic phase containes the hydroformylation catalyst component and accordingly, it is recycled to the hydroformylation of the compound having an alkenyl compound so as to reuse it without a further purification. There is not a trouble even though a part of the alcohol is incorporated in the organic phase. If necessary, it can be extracted with water.

On the other hand, the object alcohol can be obtained by the conventional method such a distillation from the water phase without any special treatment.

The present invention will be illustrated by certain examples and references which are provided for purposes of illustration only and are not intended to be limiting the present invention.

EXAMPLE 1

Into a 300 ml. autoclave made of stainless steel equipped with an electromagnetic stirrer, 100 ml. of dioctyl phthalate and 0.2 m mole of $HRh(CO)(PPh_3)_3$ ($PPh_3$ is triphenylphosphine) and 13.0 m mole of triphenylphosphine were charged. The autoclave was purged with a mixed gas of CO and H$_2$ (a molar ratio of 1:1.15) and the same mixed gas was fed under a pressure of 4 kg/cm$^2$ (gauge) at 65° C. and 230 m mole of allyl alcohol was continuously fed during 40 minutes by a constant volume pump. After the feeding of the allyl alcohol, the reaction condition was kept for 20 minutes to accomplish the reaction.

The unreacted mixed gas was purged and the product and the unreacted allyl alcohol included in the mixed gas of CO and H$_2$ and collected by a dry-ice-methanol trap were mixed with the reaction mixture and analyzed by a gas chromatography. A conversion of allyl alcohol was 98.0% and 173.8 m mole of 4-hydroxybutylaldehyde, 30.2 m mole of 2-methyl-3hydroxypropionaldehyde, 15.8 m mole of propionaldehyde, 5.5 m mole of n-propanol and a trace of butanediol were found.

In the autoclave containing the reaction mixture obtained by the hydroformylation was purged with hydrogen gas and 1.8 g. of Raney nickel and 37.0 g. of water were added and hydrogenation was carried out at 80° C. under a hydrogen pressure of 20 kg/cm² for 2 hours.

The reaction mixture discharged from the autoclave was kept in stand-still in a nitrogen atmosphere to separate the upper phase of dioctyl phthalate from the lower phase of water. The dioctyl phthalate phase contained the hydroformylation catalyst component together with 1.6 m mole of 1,4-butanediol, 0.3 m mole of 2-methyl-1,3-propanediol and a trace of n-propanol which were found by a gas chromatography. On the other hand, the water phase was filtered to separate the Raney nickel and analyzed by a gas chromatography to find 171.8 m mole of 1,4-butanediol, 29.7 m mole of 2-methyl-1,3-propanediol and 25.5 m mole of n-propanol. As a result, the yields of butanediols are 75.4% of 1,4-butanediol and 13.0% of 2methyl-1,3-propanediol based on the starting material of allyl alcohol.

The concentration of rhodium metal component in the water phase was analyzed by a flameless atomic absorptiometric method to find 0.07 ppm.

EXAMPLE 2

In accordance with the process of Example 1, the hydroformylation and the hydrogenation were carried out and the separated organic phase containing the hydroformylation catalyst component was repeatedly used for four times of the combinations of the hydroformylation and the hydrogenation. The amounts of the product of butanediols and concentrations of the dissolved rhodium component in each of the repeated operations are as follows.

| Reaction times | Amounts of butanediols in water phase | | Concentration of dissolved Rh (ppm) |
|---|---|---|---|
| | 1,4-form (m mole) | 1,3-form (m mole) | |
| 1 | 172.0 | 28.8 | 0.06 |
| 2 | 174.5 | 30.0 | 0.05 |
| 3 | 173.7 | 26.5 | 0.07 |
| 4 | 173.0 | 29.0 | 0.06 |
| 5 | 174.0 | 32.1 | 0.05 |

Note:
1,4-form: 1,4-butanediol
1,3-form: 2-methyl-1,3-propanediol

REFERENCE 1

In accordance with the process of Example 1 except that water was not added before the hydrogenation, the hydroformylation and the hydrogenation of allyl alcohol were carried out. The absorption velocity of hydrogen gas in the hydrogenation was remarkably slow. After 2 hours, the yields of butanediols were 10.5% of 1,4-butanediol and 1.7% of 2-methyl-1,3propanediol.

In the reaction mixture, a heavy oil considered as the condensed products was found together with the unreacted hydroxybutylaldehyde.

REFERENCE 2

In accordance with the process of Example 1, the hydroformylation of allyl alcohol was carried out and 37 g. of water was added to the reaction mixture and the mixture was thoroughly stirred and kept in stand-still to separate the organic phase from the water phase. Both phases were analyzed by a gas chromatography. As a result, the organic phase contained 16.2 m mole of 4-hydroxybutyaldehyde, 4.0 m mole of 2-methyl-3-hydroxypropionaldehyde 6.9 m mole of propionaldehyde, 1.3 m mole of n-prpanol and 0.8 m mole of allyl alcohol and the water phase contained 158.0 m mole of 4-hydroxybutylaldehyde, 23.8 m mole of 2methyl- 3-hydroxypropionaldehyde, 8.2 m mole of propionaldehyde, 3.4 m mole of n-propanol, 3.3 m mole of allyl alcohol and a trace of butanediols. The concentration of the rhodium component in the water phase was 0.4 ppm.

The organic phase contained a large amount of aldehydes and the water phase contained the rhodium component for several times in comparison with the result of Example 1.

EXAMPLE 3

In the autoclave of Example 1, 0.15 m mole of HRh(CO)[P($\phi$CH₃)₃]₃(P($\phi$CH₃)₃: tritolyphosphine), as a catalyst 15 m mole of tritolyphosphine and 100 ml. of toluene as a solvent were charged and a mixed gas of CO and H₂ (molar ratio of 1:1) wasfed at a reaction temperature of 135° to 140° C. under a mixed gas pressure of 8 kg/cm² and 200 m mole of ethylene was continously fed to carry out a hydroformylation.

In accordance with the process of Example 1, 2 g. of Raney nickel and 40 g. of water were added to the reaction mixture and a hydrogenation was carried out under a hydrogen pressure of 20 kg/cm² at 60° C. for 2 hours. After the reaction, the yields of n-propanol in the organic phase and the water were analyzed by a gas chromatography to find 86.1 m mole in the organic phase and 105.3 m mole in the water phase. A conversion of ethylene to n-propanol was 95.7%.

EXAMPLES 4 TO 6

In accordance with the process of Example 1, each hydroformylation was carried out by using 0.5 m mole of HRh(CO)(PPh₃)₃ as a catalyst, 15.0 m mole of triphenylphosphine under a pressure of a mixed gas of CO and H₂ (molar ratio of 1:1) of 20 kg/cm² at lower than 100° C. and 250 m mole of each olefin and 100 ml. of each solvent shown in the following table.

In accordance with the process of Example 1, each hydrogenation was carried out under each reaction condition shown in the following table. The yields of alcohols which have one more carbon atom are shown in the following table. The concentrations of the rhodium component dissolved in the water phase were substantially the same as those of Examples 1 and 2. The organic phases containing the hydroformylation catalyst could be repeatedly used.

TABLE

| | Example 4 | Example 5 | Example 6 |
|---|---|---|---|
| Olefin | allyl acetate | ethyl vinyl ether | 2-methyl-1-butene-4-ol |
| Solvent | benzene | dibutyl phthalate | anisole |
| Water (g) | 10 | 150 | 110 |
| Hydrogenation catalyst (g) | Raney nickel 1.0 | Raney nickel 1.0 | Raney nickel 1.1 |
| Hydrogen pressure (kg/cm²) | 20 | 30 | 50 |
| Temperature (°C.) | 80 | 60 | 100 |
| Time (hr.) | 1.0 | 1.0 | 5.0 |

TABLE-continued

|  | Example 4 | Example 5 | Example 6 |
|---|---|---|---|
| Yield of alcohol* (%) | 36.7 | 86.5 | 82.1 |

Note:
*Alcohols: (in Table)
Allyl acetate → acetoxybutanol and trace of 3-acetoxy-2-methylpropanol-2-acetoxybutanol.
Ethyl vinyl ether → propyleneglycol monoethyl ethers 2-Methyl-1-butene-4-ol → 3-methylpentane-1,5-diol and 2,2-dimethyl-1,4-butanediol.

We claim:

1. In a process for producing an alcohol from a compound having an alkenyl group by a hydroformylation of said compound having an alkenyl group in a substantially water immiscible solvent in the presence of a hydroformylation catalyst which is soluble in said solvent and a hydrogenation of the reaction mixture in the presence of a hydrogenation catalyst, an improvement characterized in that water is added at a ratio of 0.5 to 30 times by weight based on an aldehyde produced by said hydroformylation before said hydrogenation, and an organic phase containing the hydroformylation catalyst component is separated from a water phase containing the alcohol produced by said hydrogenation and said organic phase is recycled into said hydroformylation.

2. A process for producing an alcohol according to claim 1 wherein said hydroformylation catalyst is a rhodium complex.

3. A process for producing an alcohol according to claim 1 or 2 wherein excess of an organic tertiary phosphine is added to said hydroformylation catalyst.

4. A process for producing an alcohol according to claim 1 wherein said hydrogenation catalyst is nickel, cobalt, palladium, platinum, ruthenium type catalyst.

5. A process for producing an alcohol according to claim 1 wherein said compound having an alkenyl group is an aliphatic olefin, a hydroxyolefin, an olefin ether or an olefin ester and the corresponding saturated alcohol having one more carbon atom is produced.

6. A process for producing an alcohol according to claim 1 wherein said hydroformylation is carried out by using CO and $H_2$ at a molar ratio of 1:10 to 10:1 with or without an inert gas under a pressure of 0 to 50 $kg/cm^2$(gauge).

7. A process for producing an alcohol according to claim 1 wherein said hydrogenation is carried out by adding water to the reaction mixture obtained by said hydroformylation and feeding hydrogen under a hydrogen pressure of 5 to 100 $kg/cm^2$ (gauge) in the presence of the hydrogenation catalyst.

8. A process for producing an alcohol according to claim 1 wherein said organic phase is separated in an inert gas atmosphere so as to impart catalytic activity of the formylation catalyst and the hydrogenation catalyst.

* * * * *